United States Patent [19]

Kelly-Fry et al.

[11] Patent Number: 4,872,346
[45] Date of Patent: Oct. 10, 1989

[54] MULTIPLE FREQUENCIES FROM SINGLE CRYSTAL

[75] Inventors: Elizabeth Kelly-Fry; Steven T. Morris, both of Indianapolis, Ind.

[73] Assignee: Indianapolis Center for Advanced Research, Indianapolis, Ind.

[21] Appl. No.: 214,847

[22] Filed: Jun. 30, 1988

Related U.S. Application Data

[63] Continuation of Ser. No. 888,023, Jul. 18, 1986, abandoned.

[51] Int. Cl.⁴ ............................................ G01N 29/00
[52] U.S. Cl. ..................................................... 73/627
[58] Field of Search ................. 73/615, 627, 629, 642; 128/660

[56] References Cited

U.S. PATENT DOCUMENTS

| | | | |
|---|---|---|---|
| 2,769,158 | 10/1956 | Schultz | 73/627 |
| 3,233,450 | 2/1966 | Fry | 73/629 |
| 3,309,914 | 3/1967 | Weighart | 73/615 |
| 3,898,840 | 8/1975 | McElroy | 73/642 |
| 3,924,454 | 12/1975 | McElroy et al. | 73/642 |
| 4,257,271 | 3/1981 | Glenn | 128/660 |

Primary Examiner—Stewart J. Levy
Assistant Examiner—Louis M. Arana
Attorney, Agent, or Firm—Barnes & Thornburg

[57] ABSTRACT

A method and an apparatus for ultrasound imaging at different frequencies using a single ultrasound transducer. The transducer has a single characteristic frequency. The method and apparatus involve driving the transducer with pulses having different rise times through different coupling circuits having different impedance characteristics. Between pulses, the same transducer and coupling circuit which were used during the pulse transmission "listen" for echoes from the structure being ultrasonically investigated. It is believed that the combination of different pulses having different rise times and different coupling circuits having different characteristics enhances different ones of the frequencies contained in the Fourier spectrum of the driving pulse and suppresses others. This enables the operator to investigate a structure ultrasonically with a single transducer at different frequencies which illuminate different characteristics of the structure to greatest advantage.

15 Claims, 2 Drawing Sheets

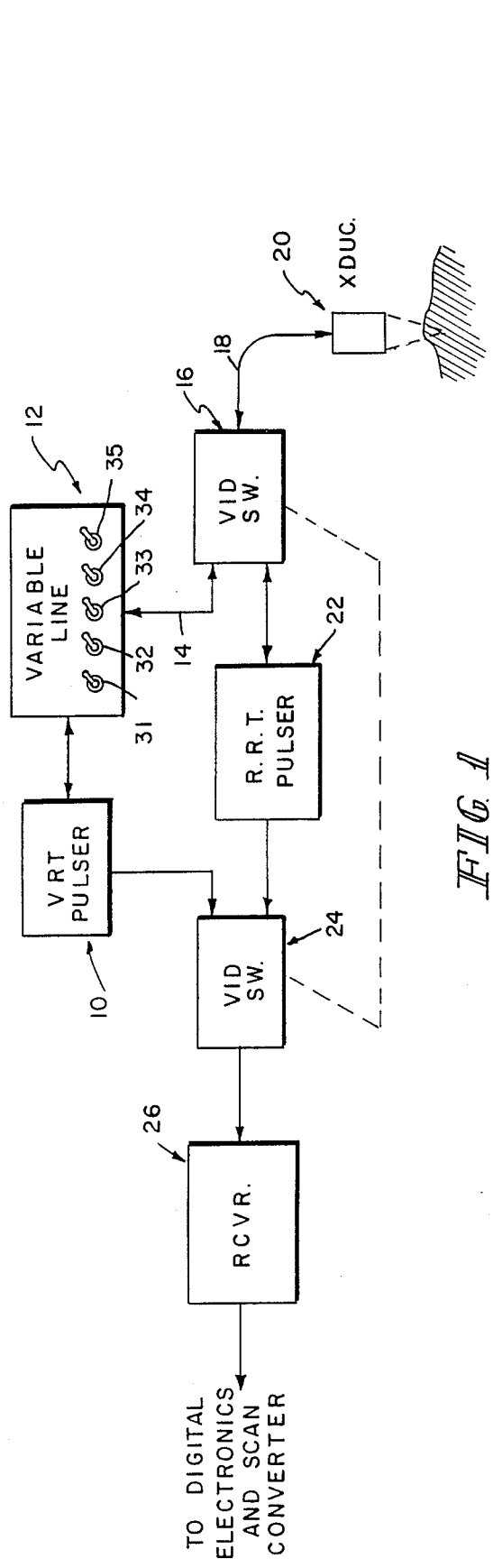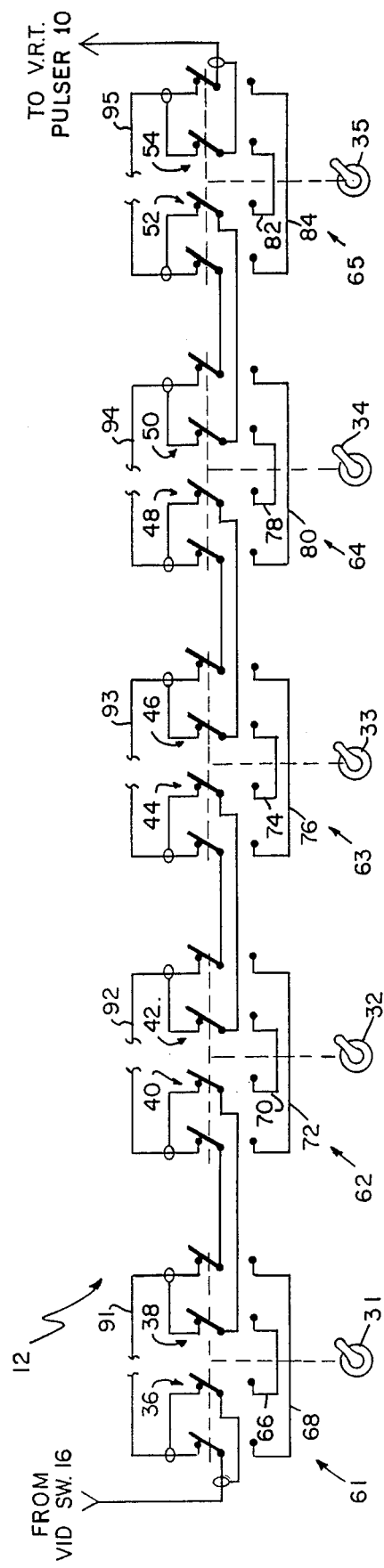

MULTIPLE FREQUENCIES FROM SINGLE CRYSTAL

This application is a continuation of application Ser. No. 888,023, filed July 18, 1986, now abandoned.

This invention relates to ultrasound imaging systems and methods of application. The invention is disclosed in the context of characterization of biological tissue, although it is believed useful in other environments as well.

In clinical breast examination, for example, detailed analysis of symptomatic patients, examination of images produced by exposure of breast tissue to ultrasound waves produced by ultrasound transducers is useful for an experienced operator to detect and characterize a particular region as a malignant tumor or a benign one. However, at all frequencies normally used for breast examination, it is sometimes difficult to detect a malignant tumor, particularly if it is a small mass and it is surrounded by fatty tissue. This is so because, at the particular standard frequency in use, the ultrasound may be scattered by the surrounding normal tissue to about the same degree as that of the malignant tumor tissue, i.e., at that frequency there is not a significant difference in their acoustic scattering coefficients. Therefore, there is insufficient contrast between the image of the tumor and the surrounding normal tissue to allow detection by imaging. Additionally if a solid tumor is detected at a standard ultrasound frequency, it is not always possible to determine if the tumor is benign or malignant on the basis of its image characteristics at that ultrasound frequency. This is so because at the standard operating frequency, the image characteristics which differentiate benign from malignant tissue (wall and internal echo characteristics, degree of attenuation of the sound, etc.) may, in certain cases, appear the same for both types of tissue. However, if the patient can be quickly examined at more than one frequency, both detection and diagnosis of malignant tumors can be improved including the detection of small malignant masses, such as early breast cancer. This is so because it has been shown that the scattering coefficient of fat is more frequency dependent than that of some malignant breast masses (F. S. Foster, M. Strban and G. Austin, "The Ultrasound Macroscope: Initial Studies of Breast Tissue", *Ultrasonic Imaging* 6, 243–261 (1984)), and that this frequency dependence allows improved detection of malignant masses when a higher ultrasound frequency is applied. (Valerie P. Jackson, M.D. et al., "Automated Breast Sonography Using a 7.5-MHz PVDF Transducer: Preliminary Clinical Evaluation", *Radiology*, Vol. 159, No. 3, Pages 679–684, June, 1986)). It has also been shown that at high frequencies malignant masses can be differentiated from benign masses because the walls of malignant masses show unique imaging characteristics due to scattering of the ultrasound by these malignant wall structures. (Y. Takehara et al., "Ultrasonic Diagnosis of early Breast Carcinoma—Advantages of High-Frequency Transducer", *Ultrasonic Examination of the Breast*, pages 83–88, 1983). Finally, it has been shown by many investigators that the ultrasound attenuation characteristics of a tumor are specifically related to its benign or malignant character. (E. Kelly Fry, et al., "Possible Misdiagnosis of Sound Attenuating Breast Masses ad Detected by Ultrasound Visualization Techniques and Solutions to this Problem", In *Proceedings*, 1978 Twenty-Third Annual Meeting of the American Institute of Ultrasound in Medicine, Vol. 1, October 19–23, San Diego, CA, p. 129; E. Kelly-Fry et al., "Factors Critical to Highly Accurate Diagnoses of Malignant Breast Pathologies by Ultrasound Imaging", *Ultrasound '82*, pp. 415–421, 1983). Thus exposure of different tissue types to different ultrasound frequencies yields different image characteristics which should allow both improved detection and diagnosis of malignant and benign tumors, This improvement in detection may be accomplished because of (1) the change in contrast between normal tissue surrounding a benign or malignant mass which accompanies a frequency change in the examining sound beam, (2) the increasing attenuation of the ultrasound at the higher frequencies, and (3) the changed image characteristics of malignant masses at high frequencies due to scattering (a halo effect around the tumor). The improvement in diagnosis may be accomplished by: (1) recognition of the specific image characteristics that are associated with malignant tumors and that are dependent on the scattering at high frequencies, of the small (in respect to wavelength of the ultrasound) tissue structures associated with the malignant process; (2) evaluation of the image characteristics associated with scattering characteristics of benign and malignant tumors at different frequencies in combination with the variation in ultrasound attenuation characteristics of benign and malignant masses at different frequencies. (The evaluation of attenuation characteristics may be based on qualitative image characteristics or on quantitative measurements). It should be understood that it is not an advantage to carry out a total examination at a high frequency only because attenuation of the ultrasound at such frequencies may not allow full penetration of the organ under examination.

The conditions outlined above should allow a skilled operator to recognize the presence of an abnormal tissue by observing the changes in images as the frequency of the sound in changed. However, this discrimination process is, by its nature, highly subjective. Further, the differences between images generated by an ultrasound transducer operating at one center frequency and those generated by another transducer operating at another center frequency are most reliable only if all other variables in the image-generating process are substantially unchanged. For example, movement by the patient undergoing examination may result in a small malignant tumorous region no longer being located beneath the transducer which is receiving the ultrasound reflections. This may result in what the operator had previously identified as possibly malignant tumorous tissue showing reflective characteristics which are interpreted by the operator as normal or benign tumorous tissue. If an operator is required to move one transducer having one characteristic center frequency aside and move another transducer having a different center frequency into position over the region of interest, the effect of this technique may also be lost because of even slight relative misalignment by the operator between the locations of the first and second transducers during their respective portions of the investigation process. It should also be realized that time required for changing transducers prolongs the clinical examination.

According to aspects of this invention a method and apparatus are provided for generating multiple non-harmonically related ultrasound frequencies from a single transducer. This enables a skilled clinician to investigate tissue at different frequencies in order to characterize tissue types qualitatively with a reasonable degree of certainty.

In accordance with one aspect of the invention, a method of ultrasound imaging of a material comprises the step of generating an electrical pulse having a first rate of rise in absolute magnitude. The rate of rise may be in either the positive or negative sense. That is, the pulse may be either positive-going or negative-going, respectively. As used herein, both cases are covered by the description of "a rate of rise in absolute magnitude," or simply by the shorter description "a rate of rise." The method further includes the steps of coupling the pulse through a modifying network to an ultrasound transducer having a characteristic center frequency for conversion into an acoustical pulse having a characteristic corresponding to the first rate of rise, receiving echoes of the acoustical pulse, and coupling the echoes to signal processing circuitry for characterization of the material based upon the echoes.

According to another aspect of the invention, a method of ultrasound imaging of a material comprises the steps of generating an electrical pulse having a first rate of rise in absolute magnitude, coupling the pulse to an acoustical transducer for conversion into an acoustical pulse, receiving echoes of the acoustical pulse, and coupling echo-related signals through a modifying network to signal processing circuitry.

According to another aspect of the invention, apparatus for ultrasound imaging of a material comprises means for generating an electrical pulse having a first rate of rise in absolute magnitude, a modifying network and means for coupling the pulse generating means to the modifying network. The apparatus further includes an acoustic transducer, means for coupling the modifying network to the transducer, signal processing circuitry for characterization of the material based upon return echoes, and means for coupling the return echoes to the signal processing circuitry.

According to yet another aspect of the invention, apparatus for ultrasound imaging of a material comprises means for generating an electrical pulse having a first rate of rise in absolute magnitude, an acoustical transducer, means for coupling the means for generating the electrical pulse to the transducer, means for receiving acoustical echoes, signal processing circuitry, and a modifying network for coupling the echo-receiving means to the signal processing circuitry. According to another aspect of the invention, a method of ultrasound imaging of a material comprises the steps of selectively generating an electrical pulse having a first rate of rise in absolute magnitude or an electrical pulse having a second, relatively longer rate of rise in absolute magnitude, coupling the electrical pulse to an acoustical transducer, receiving echoes of the acoustical pulse, and coupling echo-related signals to signal processing circuitry.

According to yet another aspect of the invention, apparatus for ultrasound imaging of a material comprises means for selectively generating an electrical pulse having a first rate of rise in absolute magnitude or an electrical pulse having a second, relatively longer rate of rise in absolute magnitude, an acoustical transducer, means for coupling the pulse generating means to the transducer for conversion into an acoustical pulse, means for receiving echoes of the acoustical pulse, signal processing circuitry, and means for coupling the means for receiving echoes to the signal processing circuitry.

The invention may best be understood by referring to the following description and accompanying drawings which illustrate the invention. In the drawings:

FIG. 1 illustrates a block diagram of an ultrasound imaging system incorporating the apparatus of the invention for practicing the method of the invention;

FIG. 2 illustrates an electrical schematic of a detail of the invention; and,

Figure 3:
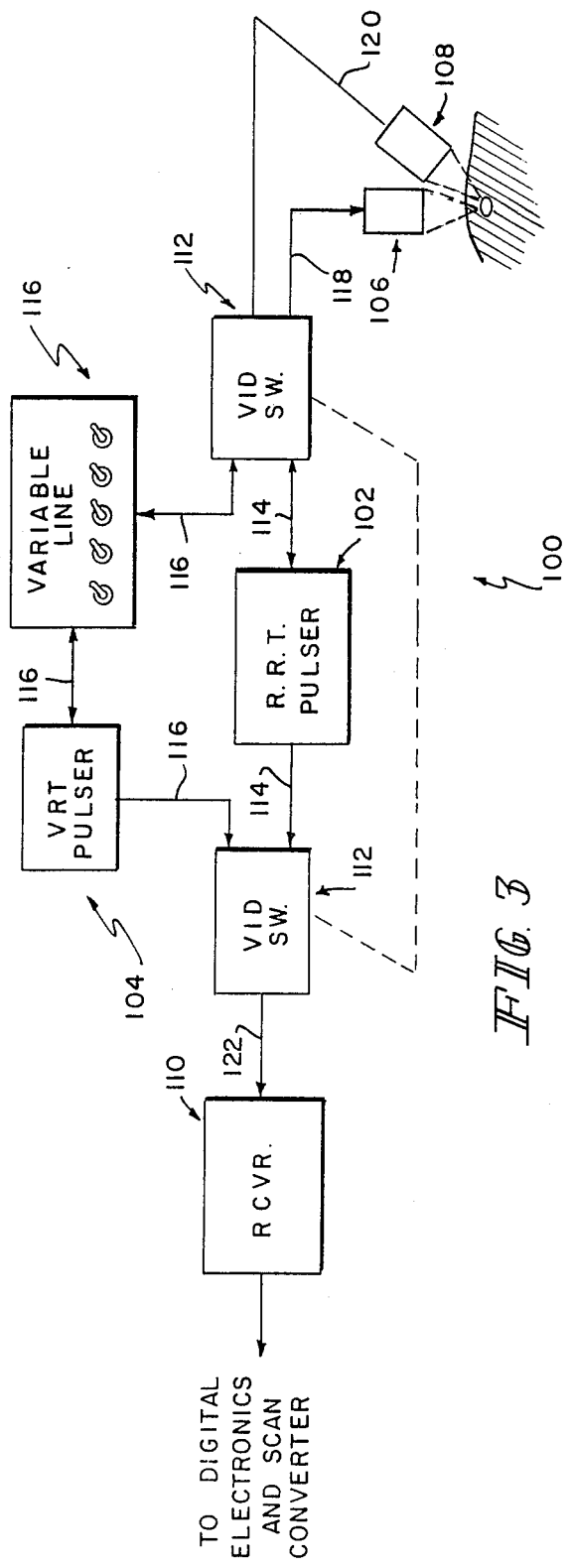
FIG. 3 illustrates a block diagram of an ultrasound imaging system incorporating the apparatus of the invention for practicing the method of the invention.

Referring now particularly to FIG. 1, an ultrasound pulser 10, such as the model 909118-3 pulser available from Labsonics, Inc., 156 East Harrison Street, Mooresville, Indiana 46158, is coupled by a short length of cable, such as RG58 cable, to a cable length select switch box 12. A one hundred-fifty inch (approximately 381 cm.) length 14 of RG58 cable couples the cable length select switch box 12 to a switch box 16. Switch box 16 is a radio-frequency switch which is available from, for example, a Panasonic video casette recorder. A forty inch (approximately 102 cm.) length 18 of RG58 cable couples the switch box 16 to an ultrasound transducer 20. Transducer 20 can be, for example, a polyvinylidene fluoride (PVDF) transducer of the type available from Kureha Chemical Industry Co., Ltd., 1-9-11 Nihonbashi Horidome-Cho, Chuo-Ku, Tokyo, Japan.

A second pulser 22, which may be of the same type previously identified, is also coupled through a short length of RG58 cable to the switch box 16. Pulsers 10 and 22 are both coupled to a switch box 24, which can be identical to switch box 16. Switch box 24 is coupled to a receiver 26, such as a Labsonics model 909150-1 receiver, which in turn is coupled to digital electronics, a scan converter and/or other image storage and/or processing circuitry (not shown) such as a video display or video casette recorder, for example.

Referring to FIG. 2, the construction of cable length select switch box 12 will be explained. Cable length select switch box 12 illustratively includes five external manual switches 31-35. Each of switches 31-35 is connected so that it operates two double-pole, double-throw switches 36, 38; 40, 42; 44, 46; 48, 50; and 52, 54 in a respective one of five sections 61-65 of cable length select switch box 12. A pair of short jumpers 66, 68; 70, 72; 74, 76; 78, 80; 82, 84 couples one pair of stationary terminals of one of the two switches 36, 40, 44, 48, 52 in each section 61-65 to a pair of stationary terminals of the other 38, 42, 46, 50, 54 of the two switches in that section 61-65.

The remaining pair of stationary terminals of one of the two switches 36, 40, 44, 48, 52 in each section 61-65 is coupled through a length 91-95, respectively, of RG58 cable to the remaining pair of stationary terminals of the other of the two switches 38, 42, 46, 50, 54 in that section 61-65. Thus, with any one of the switches 31-35 in the upper position, the drive pulses from pulser 10 to transducer 20, and the echo-related electrical signals returning from the transducer 20 by way of the one-hundred fifty inch line 14 are coupled through the length of the one or more of cable sections 91-95 which is or are switched into circuit between switch boxes 16, 24 in the channel containing cable length select switch box 12. With any one of the switches 31-35 in the lower position, that switch's respective section 61-65 is by-passed so that drive pulses from pulser 10 to transducer 20, and echo-related electrical signals returning from the transducer 20 by way of the one-hundred fifty inch line 14 do not pass through the appreciable length of line 91–95 coupled to that section 61–65 of the cable length select switch box 12. Illustrative lengths for cable sections 91–95 are two feet (approximately 0.61 meters), four feet (approximately 1.22 meters), eight feet (approximately 2.44 meters), sixteen feet (approximately 4.88 meters) and sixteen feet, respectively. This permits a length of cable as short as one-hundred ninety inches (approximately 4.83 meters—the combined lengths of cable sections 14, 18) or as long as sixty-one feet, ten inches (approximately 18.85 meters—the combined lengths of cable sections 14, 18 and 91–95) between generation of a drive pulse by pulser 10 and generation of a corresponding ultrasound pulse by transducer 20, and between receipt of an echo at transducer 20 and return of the echo-related signal to the pulser 10 side of cable length select switch box 12.

Variable rise time pulser 10 illustratively has two selectable rise times in absolute magnitude for the drive signals to transducer 20. These rise times are nominally 20 nsec. and 200 nsec. Pulser 10 can be adjusted to provide pulses with either of these nominal rise times to transducer 20. On rapid rise time pulser 24, illustratively only one rise time is used, although pulser 24 may be identical to pulser 10. The rise time of the drive signal provided by pulser 24 is nominally 20 nsec. Both of pulsers 10, 24 contain wide-band radio-frequency pre-amplifiers for the return echo-related signals passing through them from transducer 20 toward the ultrasound image-processing circuitry including receiver 26 and equipment beyond it.

Switch boxes 16, 24 are ganged so that switching of one of boxes 16, 24 from the channel containing pulser 10 to the channel containing pulser 22 or vice versa switches the other of boxes 16, 24 to this channel also. Thus, the signal flow from one of pulsers 10, 22 out of the transducer 20 and the return of echo-related electrical signals through the channel containing that pulser 10, 22 to the ultrasound image processing circuitry is controlled by the switch 16, 24 positions so that the return echo-related signals from the transducer 20 follow the same path back through one of pulsers 10, 22 that the electrical pulses which drive the transducer 20 follow to arrive at the transducer.

An analysis of a laboratory system of this general type in operation with a spectrum analyzer confirms that the center frequency of the return echo-related signals arriving at the image-processing circuitry including receiver 26 is shifted downward as additional length of line is inserted between the transducer 20 and the receiver 26. The shift in center frequency is also related to the rise time in absolute mangitude of the drive pulse from a selected one of pulsers 10, 22 provided to the transducer 20. For example, it was found that, with a transducer as identified above, having a nominal design center frequency of approximately 7.5 MHz, excitation of the transducer 20 from pulser 22 with the nominal 20 nsec. rise time pulse through only length 18 of cable (approximately 40 inches—about one meter) yields echoes having a center frequency of about 7.5 MHz. Switching of switches 16, 24 to their other positions switches the channel containing pulser 10 and cable length select switch box 12 into the circuit and pulser 22 out of circuit. With the switches 16, 24 in this position, pulser 10 set to provide 20 nsec. nominal rise time drive pulses to the transducer 20, and switches 31, 33, 34 and 35 set to provide an additional forty-two feet (about 12.8 meters) of cable length for a total of approximately fifty-eight and one-half feet (about 17.83 meters) between pulser 10 and transducer 20, the system yields return echo-related signals with a center frequency of approximately 6.5 MHz. With pulser 10 set to provide 200 nsec. nominal rise time drive pulses to transducer 20 and switches 31–35 all in the "down" positions so that the signals from pulser 10 to transducer 20 and vice versa pass through cable length select switch box 12 essentially without any additional cable length added to their path, the system provides return echo-related signals with a center frequency of approximately 4.5 MHz. With pulser 10 set to provide 200 nsec. nominal rise time drive pulses to transducer 20 and switches 31, 32 and 33 thrown to provide an additional fourteen feet (approximately 4.27 meters) of cable length for a total of about twenty-nine feet, ten inches (approximately 9.09 meters) between pulser 10 and transducer 20, the system yields return echo-related signals with a center frequency of approximately 3.5 MHz. Other center frequencies can be obtained by other combinations of switches 31–35 and the two alternate settings for rise time of the drive signal from pulser 10.

Referring now to FIG. 3, an apparatus 100 for ultrasound imaging of a material comprises first means 102 for generating an electrical pulse having a first rate of rise in absolute magnitude, second means 104 for generating an electrical pulse having a second, relatively longer rate of rise in absolute magnitude, an acoustical transducer 106, means 108 for receiving acoustical echoes, signal processing circuitry 110, switching means 112, means 114, 116 for coupling the first 102 and second 104 means, respectively, for generating an electrical pulse to the switching means 112, means 118 for coupling the transducer 106 to the switching means 112, means 120 for coupling the means 108 for receiving acoustical echoes to the switching means 112 and means 122 for coupling the signal processing circuitry 110 to the switching means 112. The switching means 112 has a first position in which the first means 102 for generating an electrical pulse is in circuit with the transducer 106, the means 108 for receiving acoustical echoes and the signal processing circuitry 110, and a second position in which the second means 104 for generating an electrical pulse is in circuit with the transducer 106, the means 108 for receiving acoustical echoes and the signal processing circuitry 100.

Thus it will be appreciated that the illustrated system permits the skilled operator to obtain ultrasound tissue images at different frequencies which facilitates characterization of the tissues thus imaged as malignant or benign.

What is claimed is:

1. A method of ultrasound imaging of a material, the method comprising the steps of selectively generating an electrical pulse having a first rate of rise in absolute magnitude or an electrical pulse having a second, relatively longer rate of rise in absolute magnitude, coupling the electrical pulse through a modifying network to an acoustical transducer for conversion into an acoustical pulse, receiving echoes of the acoustical pulse, and coupling echo-related signals to signal processing circuitry.

2. The method of claim 1 wherein the step of coupling the electrical pulse through a modifying network to the transducer comprises the step of coupling the means for generating the electrical pulse through one of multiple, selectable, different length paths to the transducer.

3. A method of ultrasound imaging of a material, the method comprising the steps of selectively generating an electrical pulse having a first rate of rise in absolute magnitude or an electrical pulse having a second, relatively longer rate of rise in absolute magnitude, coupling the electrical pulse to an acoustical transducer for conversion into an acoustical pulse, receiving echoes of the acoustical pulse, and coupling echo-related signals through a modifying network to signal processing circuitry.

4. The method of claim 3 wherein the step of coupling echo-related signals through a modifying network to signal processing circuitry comprises the steps of receiving the echoes through the transducer and coupling the transducer through one of multiple, selectable, different length paths to the signal processing circuitry.

5. Apparatus for ultrasound imaging of a material, the apparatus comprising means for selectively generating an electrical pulse having a first rate of rise in absolute magnitude or an electrical pulse having a second, relatively longer rate of rise in absolute magnitude, an acoustical transducer, a modifying network for coupling the pulse generating means to the transducer for conversion of the electrical pulse into an acoustical pulse, means for receiving echoes of the acoustical pulse, signal processing circuitry, and means for coupling the means for receiving echoes to the signal processing circuitry.

6. The apparatus of claim 5 wherein the means for coupling the means for receiving echoes to the signal processing circuitry comprises a modifying network.

7. The apparatus of claim 6 wherein the means for receiving echoes of the acoustical pulse comprises the transducer.

8. The apparatus of claim 6 wherein the modifying network for coupling the means for generating an electrical pulse to the transducer comprises the modifying network for coupling the means for receiving echoes to the signal processing circuitry.

9. The apparatus of claim 5 wherein the modifying network for coupling the means for generating an electrical pulse to the transducer comprises means for providing a plurality of selectable, different length paths between the means for generating the electrical pulse and the transducer.

10. The apparatus of claim 9 wherein the means for receiving echoes comprises the transducer and the means for coupling the means for receiving echoes to the signal processing circuitry comprises the means for providing a plurality of selectable, different length paths between the means for generating the pulse and the transducer.

11. Apparatus for ultrasound imaging of a material, the apparatus comprising means for selectively generating an electrical pulse having a first rate of rise in absolute magnitude or an electrical pulse having a second, relatively longer rate of rise in absolute magnitude, an acoustical transducer, means for coupling the pulse generating means to the transducer for conversion of the electrical pulse into an acoustical pulse, means for receiving echoes of the acoustical pulse, signal processing circuitry, and a modifying network for coupling the means for receiving echoes to the signal processing circuitry.

12. The apparatus of claim 11 wherein the modifying network comprises means for providing a plurality of selectable, different length paths between the means for receiving echoes and the signal processing circuitry.

13. The apparatus of claim 12 wherein the means for coupling the means for generating the electrical pulse to the transducer comprises a modifying network.

14. The apparatus of claim 13 wherein the means for receiving echoes comprises the transducer and the modifying network for coupling the means for generating a pulse to the transducer comprises the means for providing a plurality of selectable, different length paths between the means for receiving echoes and the signal processing circuitry.

15. Apparatus for ultrasound imaging of a material, the apparatus comprising first means for generating an electrical pulse having a first rate of rise in absolute magnitude, second means for generating an electrical pulse having a second rate of rise in absolute magnitude, an acoustical transducer, means for receiving acoustical echoes, signal processing circuitry, switching means, means for coupling the first and second means for generating an electrical pulse to the switching means, means for coupling the transducer to the switching means, means for coupling the means for receiving acoustical echoes to the switching means and means for coupling the signal processing circuitry to the switching means, the switching means having a first position in which the first means for generating an electrical pulse is in circuit with the transducer, the means for receiving acoustical echoes and the signal processing circuitry, and a second position in which the second means for generating an electrical pulse is in circuit with the transducer, the means for receiving acoustical echoes and the signal processing circuitry.

* * * * *